United States Patent [19]

Ohmoto et al.

[11] Patent Number: 5,183,755
[45] Date of Patent: Feb. 2, 1993

[54] ANTI-HUMAN PAPILLOMAVIRUS MONOCLONAL ANTIBODY, HYBRIDOMA PRODUCING THE SAME AND PROCESS FOR PREPARING THE SAME

[75] Inventors: Hiroshi Ohmoto, Osaka; Seiichi Iwamoto, Kobe, both of Japan

[73] Assignee: Kanebo, Ltd., Tokyo, Japan

[21] Appl. No.: 482,717

[22] Filed: Feb. 21, 1990

[30] Foreign Application Priority Data

Feb. 21, 1989 [JP] Japan .................................. 1-40714

[51] Int. Cl.$^5$ ....................... C12N 5/22; C12P 21/08; C07K 15/28
[52] U.S. Cl. ........................... 435/240.27; 435/70.21; 530/388.3
[58] Field of Search ........... 435/70.21, 240.27, 240.26; 530/387, 388.3; 935/104

[56] References Cited

U.S. PATENT DOCUMENTS 4,551,270 11/1985 Danos et al. .

FOREIGN PATENT DOCUMENTS 8605816 4/1985 PCT Int'l Appl. .

OTHER PUBLICATIONS

Chemical Patents Index, Basic Abstracts Journal (Derwent Publications Ltd) and partial English translation.
"Dako Rabbit Anti-Bovine Papillomavirus (BPV-1)", Dako Corporation, Catalog No. B580, p. 3.
Jenson et al., "Immunologic Relatedness of Papillomaviruses From Different Species", JNCI, vol. 64, No. 3, Mar. 1980, pp. 495–500.
Alberto Roseto, "Monoclonal antibodies to the Major Capsid Protein of Human Papillomavirus Type I", J. Gen. Virol., 65, 1984, pp. 1319–1324.
Cowsert et al., "Topographical and Conformational Epitopes of Bovine Papillomavirus Type 1 Defined by Monoclonal Antibodies", JNCI, vol. 79, No. 5, 1987, pp. 1053–1057.
Gerard Orth et al., "Evidence for Antigenic Determinants Shared by the Structural Polypeptides of (SHOPE) Rabbit Papillomavirus and Human Papillomavirus Type 1", Virology, 91, pp. 243–255.
The EMBO Journal, vol. 7, No. 3, 1988, pp. 822–833, Doorbar et al., "Analysis of HPV-1 E4 gene Expression using ipitopedifined antibodies".
Nakai et al., J. Gen. Virol., 68:189–1896, 1987.

Primary Examiner—Y. Christina Chan
Assistant Examiner—Susan L. Futrovsky
Attorney, Agent, or Firm—Wegner, Cantor, Mueller & Player

[57] ABSTRACT

An anti-human papillomavirus (HPV) monoclonal antibody reactive with various types of HPVs, which is produced by a hybridoma comprising a fused cell of a mouse spleen cell from a mouse immunized with an alkali-treated HPV type 1 (HPV-1) and a mouse myeloma cell, and which is reactive with polypeptides of about 57 kilodaltons, about 160 kilodaltons and about 230 kilodaltons of HPV-1, and a process for preparing the same. The monoclonal antibody of the invention is reactive with various types of HPV and useful for diagnosis of various types of HPV infection (primary diagnosis).

2 Claims, No Drawings

ANTI-HUMAN PAPILLOMAVIRUS MONOCLONAL ANTIBODY, HYBRIDOMA PRODUCING THE SAME AND PROCESS FOR PREPARING THE SAME

This invention relates to an anti-human papillomavirus (HPV) monoclonal antibody, a hybridoma producing said monoclonal antibody and a process for preparing said monoclonal antibody. More particularly, this invention relates to an anti-HPV monoclonal antibody reactive with various types of HPVs, which is produced by a hybridoma comprising a fused cell of a mouse spleen cell from a mouse immunized with an alkali-treated HPV type 1 (HPV-1) and a mouse myeloma cell, and which is reactive with polypeptides of about 57 kilodaltons, about 160 kilodaltons and about 230 kilodaltons of HPV-1, a hybridoma producing said monoclonal antibody and a process for preparing said monoclonal antibody. The anti-HPV monoclonal antibody of this invention is useful for diagnosis of various types of HPV infection.

TECHNICAL BACKGROUND AND PRIOR ART

Human papillomavirus (HPV) is a small DNA virus infectious to human beings which belongs to papovaviridae and is classified into various types based on base sequences of DNA thereof. Hitherto, there have been isolated and identified more than 50 types of HPV from HPV-infected tissues.

HPV infection causes a variety of diseases such as verruca vulgaris, verruca plana, myrmecia, epidermodysplasia verruciformis, condyloma acuminatum, laryngenal papillomatosis, etc. which are distinguished depending on regions of human the body at which the symptom appears, and features on shapes and tissue images thereof. Since some of these diseases become malignant and are turned into cervical cancer, squamous carcinoma and the like, a great attention has focused on the early diagnosis of HPV infectious disease. The HPV infectious disease mentioned herein is meant to include not only the various above mentioned diseases induced by the HPV infection but also conditions where HPV is carried by individuals without outbreak of disease.

HPV infection can be diagnosed by detecting an antigen-antibody reaction between an antigen in epidermal tissues taken from individuals suspected of the infection and an anti-HPV antibody.

In diagnosis of HPV infection utilizing the anti-HPV antibody, it is preferable to firstly diagnose whether there is any HPV infection by utilizing an antibody capable of reacting with various types of HPV (primary diagnosis) and then to determine the type of infecting HPV with a type-specific antibody which reacts only with a specific type of HPV (secondary diagnosis). A diagnosis utilizing only the type-specific antibody without primary diagnosis requires a large number of type-specific antibodies and wastes much time and labor since the diagnosis with the type-specific antibody requires all of more than 50 type-specific antibodies and a large amount of epidermal tissues necessary for diagnosis using each type-specific antibody.

Among known antibodies capable of reacting with various papillomaviruses (hereinafter referred to as "PV") is a rabbit anti-bovine papillomavirus (hereinafter referred to as "BPV") antibody which is a known reagent commercially available from DAKO CO. (catalogue No. B580). This antibody is obtained by immunizing a rabbit with a chemically treated bovine papillomavirus type 1 (hereinafter referred to as "BPV-1") and it has been evaluated to be capable of reacting with any of a wide variety of PVs not only BPV-1. However, the present inventors have tested this antibody for its reactivity with a variety of PVs and have found that this antibody could not detect some HPV infectious diseases as will be shown in the Experiment described hereinafter.

Another known antibody reactive with a variety of HPV is an anti-HPV antibody produced by immunizing a rabbit with a sodium dodecyl sulfate (hereinafter referred to as "SDS")-disrupted HPV (JNCI Vol. 64, pp495-500, 1980). However, it is necessary to steadily provide a large amount of HPV as an antigen for producing this antibody steadily but HPV grows only in human body and a method has not yet been established for growth of HPV in tissue culture and the like, and hence, this antibody is disadvantageous to an industrial, steady production in a large amount.

It is known that a monoclonal antibody, which is produced by forming a hybridoma of an antibody-producing cell and a cell capable of rapidly and semi-permanently proliferating such as myeloma cell, followed by culture of said hybridoma, is more advantageous than a polyclonal antibody from various points of view.

A production of an anti-HPV monoclonal antibody by a hybridoma is disclosed in European Patent Publication No. 174228A and Roseto A. et al. (J. Gen. Virol. Vol. 65, pp 1319-1324, 1984). The anti-HPV monoclonal antibodies disclosed in these references are, however, type-specific antibodies capable of reacting only with human papilloma-virus type 1 (HPV-1) and not those reactive with various other HPVs. According to the description of the literature, Western blotting of the monoclonal antibodies revealed that they reacted with 54 kilodaltons and 76 kilodaltons of polypeptides in the protein component of HPV-1.

U.S. Pat. No. 4,551,270 and PCT Application WO 8605816A also disclose an amino acid sequence of a short peptide which can be a common antigen of various HPVs and describe that a monoclonal antibody capable of reacting with various HPVs can be prepared by utilizing the peptide as an antigen. However, an anti-HPV monoclonal antibody capable of reacting with various HPVs is not actually obtained in these references.

Lex M. Cowsert et al. (JNCI, Vol. 79, No. 5, pp1053-1057, Nov. 1987) also report a monoclonal antibody produced by immunizing a mouse with an SDS-treated bovine PV; and Orth G. et al. (Virology No 1. 91, pp243-255, 1978) disclose a polyclonal antibody produced by immunizing a guinea pig with an alkali-treated HPV, said polyclonal antibody being genus specific, not type-species specific.

A novel monoclonal antibody capable of reacting with a variety of HPVs and a novel process for preparing said monoclonal antibody are still earnestly desired in the field.

BRIEF SUMMARY OF THE INVENTION

Under such circumstances, the present inventors have intensively studied to develop an anti-HPV monoclonal antibody capable of reacting with various HPVs which is useful for primary diagnosis of HPV infection, and as a result, have found that the monoclonal antibody can be obtained by alkali-treating HPV-1 to prepare an antigen, preparing a hybridoma producing an antibody against said antigen, cloning said hybridoma and selecting those hybridomas producing a monoclonal antibody reactive with various HPVs and that the monoclonal antibody thus prepared is useful for primary diagnosis of HPV infection.

An object of the invention is to provide a novel anti-HPV monoclonal antibody which is reactive with all types of HPVs and is useful for primary diagnosis of HPV infection. Another object of the invention is to provide a method for preparing said anti-HPV monoclonal antibody by a cell fusion technology. These and other objects and advantages of the invention will be apparent to those skilled in the art from the following description.

DETAILED EXPLANATION OF THE INVENTION

The novel anti-HPV monoclonal antibody reactive with various types of HPVs of this invention is produced by a hybridoma comprising a fused cell of a mouse spleen cell from a mouse immunized with an alkali-treated HPV type 1 (HPV-1) and a mouse myeloma cell, and which is reactive with polypeptides of about 57 kilodaltons, about 160 kilodaltons and about 230 kilodaltons of HPV-1, a hybridoma producing said monoclonal antibody and a process for producing said monoclonal antibody.

The method of the invention for producing the monoclonal antibody comprises:

a) treating HPV-1 with an alkali to prepare an antigen, b) fusing a spleen cell from a mouse immunized with said antigen and a mouse myeloma cell to produce a hybridoma, c) cloning said hybridoma and selecting those hybridomas producing desired anti-HPV monoclonal antibody, and d) allowing said hybridomas to grow in a culture medium or within the peritoneal cavity of a mouse, harvesting the culture supernatant or the mouse ascites and separating the desired antibody therefrom.

The hybridoma of the invention producing the monoclonal antibody has been internationally deposited on Feb. 9, 1989 at the Fermentation Research Institute Agency of Industrial Science and Technology, Tsu Kuba Science City, Ibaraki 305, Japan under Budapest Treaty under the accession number FERM BP-2278, which is designated "anti-human papillomavirus monoclonal antibody (K1H8) producing hybridoma".

Preparation of Hybridoma

The hybridoma of the invention is prepared by the following steps (A) to (E).

(A) Preparation of Antigen

Epidermal tissue infected with HPV-1 is suspended in a buffer, e.g. phosphate buffered saline (hereinafter referred to as "PBS"), ground with a grinder and centrifuged to remove cellular components to give a crude HPV-1.

The above crude HPV-1 is added to an aqueous cesium chloride solution and the mixture is subjected to density gradient centrifugation and the portion of a band having a density of 1.34 g/cm$^3$ is collected to give an HPV-1 solution. This HPV-1 solution is then dialyzed against PBS to give a solution of purified HPV-1.

The purified HPV-1 is then treated with an alkali to prepare an alkali-treated HPV-1 (antigen). The alkali treatment can be made by dialyzing the solution of the purified HPV-1 against an alkaline aqueous solution of pH 10 to 11, preferably pH of about 10.5 at about 4° C. for 10 to 20 hours. The alkaline aqueous solution used in the alkali treatment is preferably a buffer containing 2-aminoethanol.

(B) Preparation of Antibody Producing Spleen Cell

Mice (e.g. BALB/c mice, preferably of more than 6 weeks old) are immunized with an emulsion comprising the above alkali-treated HPV-1 (antigen) together with an adjuvant such as Freund's adjuvant and spleen is taken from the animals to prepare antibody producing spleen cells.

The immunization is usually carried out by administering the alkali-treated HPV-1 (antigen) to the animal at least 3 times. A dose in each administration is 1 to 1000 μg/animal of the alkali-treated HPV-1. The alkali-treated HPV-1 is preferably administered to mice in the form of an emulsion comprising an aqueous solution having a concentration of 100 to 1000 μg/ml of HPV-1 in admixture with an equivalent volume of an adjuvant (e.g. Freund's adjuvant).

After immunization, spleen is taken out from mice and spleen cells are dispersed into Dulbecco's modified Eagle's minimum medium (hereinafter referred to as "DMEM medium") to prepare a suspension of antibody producing spleen cells.

(C) Preparation of Myeloma Cells

8-Azaguanine resistant myeloma cells, for example, commercially available mouse-derived myeloma cell P3X63Ag8U.1 (hereinafter referred to as "P3U1"), Sp2/0-Ag14, P3X63-Ag8.653 etc. (all these cells are commercially available from Dainippon Pharmaceutical Co., Ltd.) are employed.

All these cells are cultured in a culture medium (e.g. RPMI 1640 medium supplemented with 5 to 20% fetal calf serum or DMEM medium supplemented with 5 to 20% fetal calf serum) containing about 100 μM 8-azaguanine at 37° C. under atmosphere containing 5 to 10% $CO_2$ and washed with a medium deficient in 8-azaguanine for use in the subsequent cell fusion.

(D) Cell Fusion and Selection of Anti-HPV Antibody Producing Hybridomas

The antibody producing spleen cells and the myeloma cells prepared above are cell-fused and those hybridomas producing an anti-HPV antibody are selected.

The cell fusion is carried out by mixing a suspension of the antibody producing spleen cells and a suspension of the myeloma cells, subjecting the mixture to a low speed centrifugation to remove supernatant to give a mixture of both antibody producing cells and myeloma cells, adding thereto a polyethylene glycol (hereinafter referred to as "PEG") solution, stirring and shaking the mixture as described in Nature, Vol. 266, p550, 1977, or by mixing the antibody producing cells, the myeloma cells and a PEG solution together and subjecting the mixture to a low speed centrifugation in accordance with the method described in Somat. Cell Genet., Vol. 3, p231, 1977.

PEG preferably has an average molecular weight of 1000 to 6000 and is preferably used as a solution in DMEM medium at a concentration of preferably 30 to 50% (w/w).

A mixing ratio of the antibody producing cells to the myeloma cells is preferably such that the amount of the antibody producing cells is 1 to 20 times larger than that of the myeloma cells.

For selection of hybridomas, the mixture of cells obtained by the above cell fusion is poured into each well of microplate, cultured in a medium where only hybridomas can grow, e.g. HAT medium (comprising hypoxanthine, aminopterin and thymidine), and selecting wells where cells grow to give hybridomas.

The culture is carried out by suspending the cell mixture obtained by the cell fusion in HAT medium at about $1 \times 10^6$ cells/ml, pouring the suspension into each well of microplate and culturing it at 37° C. under atmosphere containing 5 to 10% $CO_2$ for 10 to 14 days while replacing the medium with a fresh medium usually on the fourth day.

The anti-HPV antibody producing hybridomas are then selected by enzyme immunoassay of the culture supernatant of each hybridoma.

(E) Cloning of Hybridomas and Selection of Hybridomas of the Invention

The anti-HPV antibody producing hybridomas prepared in (D) are cloned by a limiting dilution method with HAT medium or other conventional method and those hybridomas being capable of producing an anti-HPV monoclonal antibody are selected by the enzyme immunoassay as in (D).

The anti-HPV monoclonal antibody producing hybridomas thus cloned are subjected to selection by the tissue staining procedure as described in the following Experiment where plural epidermal tissues infected with various HPVs are employed, and the anti-HPV monoclonal antibody producing hybridoma reactive with all of these tissues is selected.

The thus selected hybridoma is cultured in HT medium (medium containing hypoxanthine and thymidine) at 37° C. under atmosphere containing 5 to 10% $CO_2$ for about 1 to 2 weeks and then subcultured in a usual medium, for example RPMI 1640 medium supplemented with 5 to 20% fetal calf serum or DMEM medium supplemented with 5 to 20% fetal calf serum under the same conditions, and then stored.

The hybridoma is stored by suspending them in either RPMI 1640 medium or DMEM medium, both media being supplemented with 5 to 20% fetal calf serum and further being added with about 10% dimethyl sulfoxide (hereinafter referred to as "DMSO") under cooling with liquid nitrogen.

The thus obtained hybridoma producing the antibody reactive with all HPVs of the invention (designated "anti-human papillomavirus monoclonal antibody (K1H8) producing hybridoma") has been deposited under the accession number FERM BP-2278 as mentioned hereinbefore.

Preparation of Anti-HPV Monoclonal Antibody

The anti-HPV monoclonal antibody of the invention can be prepared by culturing the hybridoma prepared as mentioned above at 37° C. under atmosphere containing 5 to 10% $CO_2$ followed by separation and purification from the culture supernatant.

The hybridoma is cultured in RPMI 1640 medium supplemented with 5 to 20% fetal calf serum or DMEM medium supplemented with fetal calf serum for 3 days to 3 weeks, preferably for 10 to 14 days while subculturing about every about 3 days.

Alternatively, the anti-HPV monoclonal antibody of the invention can be prepared by growing the hybridoma prepared as mentioned above in the peritoneal cavity of small mammals compatible with the hybridoma such as mice (e.g. BALB/c mice), followed by separating and purifying from the ascites. The intraperitoneal growing of the hybridoma is usually carried out for 1 to 3 weeks.

The anti-HPV monoclonal antibody of the invention can be purified by centrifugation of the culture solution or the ascites, followed by salting out with ammonium sulfate or ion exchange chromatography.

Salting out is preferably carried out with a 30 to 50% saturated aqueous solution of ammonium sulfate. The monoclonal antibody salted out is then dialyzed against PBS to give a PBS solution containing the purified monoclonal antibody of the invention.

Ion exchange chromatography is preferably conducted by column chromatography with an anion exchange resin such as DEAE Sepharose (manufactured by Pharmacia, Sweden). The elution is preferably carried out with Tris buffer (pH about 7.0).

The aqueous solution of anti-HPV monoclonal antibody of the invention thus obtained can be stored after freezing or lyophilization.

The anti-HPV monoclonal antibody of the invention can be used for diagnosis of HPV infection.

Diagnosis of HPV infection can be made by detecting the reactivity of the anti-HPV monoclonal antibody of the invention and epidermal tissues or cells taken from individuals (tissue staining).

A tissue staining procedure can be conducted either by a direct procedure wherein the anti-HPV monoclonal antibody of the invention labelled with a labelling material such as biotin or fluorescein isothiocyanate (hereinafter referred to as "FITC") etc. is reacted with tissues or cells from individuals and the label is detected as a measure of the reactivity, or by an indirect procedure wherein the anti-HPV monoclonal antibody of the invention is reacted with tissues or cells from individuals and the reacted monoclonal antibody is then reacted with a secondary antibody labelled with a labelling material such as biotin or FITC, followed by detection of the label as a measure of the reactivity.

When the label is biotin, the tissues or cells are stained by an avidin-biotinylated peroxidase complex method ("Handbook of Experimental Immunology", Vol. 4, ed. by D. M. Weir, BLACKWELL SCIENTIFIC PUBLICATIONS, 129.10) and the reactivity is detected by microscopic observation. Brown stained particles are observed in those tissues or cells infected with HPV.

In case of labelling with FITC, the reactivity is detected by observation with a fluorescence microscope. Green fluorescent particles are observed in those tissues or cells infected with HPV.

The anti-HPV monoclonal antibody of the invention can detect various HPVs. For example, the anti-HPV monoclonal antibody of the invention clearly reacts with tissues infected with various HPVs such as myrmecia, verruca plana, condyloma acuminatum and the like, and thereby, the HPV infection of all samples can be tested (see Experiment described hereinbelow), which the conventional rabbit anti-BPV antibody could not detect the HPV infection in some samples. Thus, the anti-HPV monoclonal antibody of the invention is quite useful for diagnosis of HPV, particularly for diagnosis of primary diagnosis of HPV.

Experiment (Diagnosis of HPV Infection)

A diagnostic test was conducted using the anti-HPV monoclonal antibody of the invention which is subjected to an antigen-antibody reaction with tissues. The antigen-antibody reaction was detected by the avidin-biotinylated peroxidase complex method as mentioned above with staining of tissues. At the same time, commercially available rabbit anti-BPV antibody was also tested for comparison.

1. Materials (a) Specimen

The following 9 tissue specimens from individuals infected with HPV were used.

| Myrmecia | one specimen |
|---|---|
| Verruca plana | one specimen |
| Condyloma acuminatum | seven specimens (a) to (g) |

(b) Antibody

Antibody of the Invention

An aqueous solution of the anti-HPV monoclonal antibody at a concentration of 2 µg/ml which was prepared by diluting the monoclonal antibody solution obtained in Example 2 with PBS.

Reference Antibody

An aqueous solution of a rabbit anti-BPV antibody at a concentration of 10 µg/ml which was prepared by diluting the rabbit anti-BPV antibody (manufactured by DAKO CO., catalogue No. B580) with PBS.

2. Method

Specimens taken from individuals were embedded in paraffin and sliced into 5 µm pieces of width. The paraffin embedded tissue sections were each put on a slide glass and paraffin was removed in the conventional manner and thereto was added the antibody solution (0.2 ml), and the mixture was reacted at room temperature for 2 hours and washed with PBS (pH 7.4) at 4° C. three times each for 5 minutes.

Then, to the specimens were added dropwise biotin-labelled anti-mouse IgG+IgA+IgM (H+L)(0.2 ml) (manufactured by ZYMED Laboratories, Inc.) adjusted to a concentration of 5 µg/ml with PBS (pH 7.4) in case of the anti-HPV monoclonal antibody of the invention, or biotin-labelled anti-rabbit IgG (0.2 ml)(manufactured by ZYMED Laboratories, Inc.) adjusted to a concentration of 5 µg/ml with PBS (pH 7.4) in case of the rabbit anti-BPV antibody, and the mixture was reacted at room temperature for 1 hour and washed with PBS (pH 7.4) at 4° C. three times each for 5 minutes.

The avidin-biotinylated peroxidase complex solution (0.2 ml)(Vectastain ®, manufactured by Vector Laboratories, Inc.) was then added dropwise to the specimens, and the mixture was reacted at room temperature for 30 minutes and washed with PBS (pH 7.4) at 4° C. three times each for 5 minutes.

Then, to the specimens were added dropwise each 0.2 ml of PBS (pH 7.4) containing 3,3'-diaminobenzidine.4HCl (0.2 mg/ml) and 0.015% (w/v) hydrogen peroxide, and the mixture was reacted at room temperature for 30 minutes and the reaction was quenched with addition of distilled water.

Finally, one to two drops of a PBS solution containing 50% (v/v) glycerol was added to the specimens and, after covering with a cover glass, developed color images were observed with a microscope. Those specimens taken from individuals infected with HPV revealed brown stained particles. The staining was graded as follows:

| | |
|---|---|
| +: | 1 to 5 stained particles |
| ++: | 6 to 30 stained particles |
| +++: | Not less than 31 stained particles |
| −: | No stained particles |
| ±: | Unclearly stained particles |

3. Results

The results are shown in Table 1.

TABLE 1

| | Antibody (Ab) | |
|---|---|---|
| Specimens | Ab of the invention (K1H8) | Rabbit anti-BPV Ab (Control) |
| Myrmecia | ++ | +++ |
| Verruca plana | +++ | ++ |
| Condyloma acuminatum (a) | ++ | +++ |
| Condyloma acuminatum (b) | + | − |
| Condyloma acuminatum (c) | + | ± |
| Condyloma acuminatum (d) | ++ | ++ |
| Condyloma acuminatum (e) | + | + |
| Condyloma acuminatum (f) | +++ | +++ |
| Condyloma acuminatum (g) | +++ | +++ |

As is clearly shown in Table 1, the anti-HPV monoclonal antibody of the invention could detect all of the HPV infectious diseases tested while the commercially available rabbit anti-BPV antibody could not detect some HPV infectious diseases.

This invention is more specifically illustrated by the following Examples but should not be construed to be limited thereto. In Examples, percentage means % (v/v) unless otherwise mentioned.

EXAMPLE 1

(a) Preparation of Hybridoma)

The hybridoma of the invention was obtained by the following procedures (a) to (e).

(a) Preparation of Antigens

Wart tissue infected with HPV-1 (5 g) was added to PBS (pH 7.4; 50 ml), ground with a grinder and centrifuged at a low speed (1000 rpm; 10 minutes). The resultant supernatant was then centrifuged at a high speed (10,000 rpm; 10 minutes) to give precipitate of crude HPV-1. The obtained crude HPV-1 was then overlayed on an aqueous solution of cesium chloride (density: 1.34 g/cm$^3$) and subjected to a density gradient centrifugation (30,000 rpm; 20 hours) with SW41Ti Rotor (manufactured by Beckmann CO.,). A band having a density of 1.34 g/cm$^3$ was separated and dialyzed against PBS (1000 ml) at 4° C. for 16 hours to prepare a solution of a purified HPV-1 in PBS (1 ml).

A mixture of 5 M NaCl (12 ml), 2M Tris(hydroxymethyl)aminomethane-HCl (pH 7.5; 4 ml) and 250 mM ethylenediamine tetraacetate (hereinafter referred to as "EDTA"; 1.6 ml) was diluted with distilled water to make a total amount of 500 ml and pH thereof was adjusted to 10.5 by addition of 2-aminoethanol to prepare a dialysis solution. The purified HPV-1 prepared as mentioned above was dialyzed against this dialysis solution at 4° C. for 16 hours, followed by dialysis against a dialysis solution comprising 1 mM EDTA-10 mM Tris(hydroxymethyl)aminomethane -HCl (pH 8.0; 500 ml) at 4° C. for 16 hours to give 1 ml of a solution (density; 500 μg/ml) of an alkali-treated HPV-1 (antigen).

(b) Preparation of Antibody Producing Spleen Cells

The alkali-treated HPV-1 solution (250 μl; containing about 125 μg of the alkali-treated HPV-1) was mixed with an equivalent volume of complete Freund's adjuvant (manufactured by Difco Laboratories, Inc.) to prepare an emulsion. Female BALB/c mouse of 9 weeks old was subjected to the primary immunization by administering the emulsion subcutaneously (490 μl) and at footpads (10 μl). After 14 days, the animal was boostered with an emulsion comprising the alkali-treated HPV-1 and incomplete Freund's adjuvant in the same manner. Fourteen days after the booster injection, the animal was given intravenous administration of a physiological saline solution (200 μl) of the above alkali-treated HPV-1 (about 10 μg) for final immunization. After 3 days, the mouse was sacrificed and the spleen was aseptically taken out. The spleen was cut with scissors in DMEM medium and passed through a mesh to prepare a suspension of a single cell. The resultant suspension was washed with DMEM medium ($\times 3$) to prepare a suspension of the antibody-producing spleen cells in DMEM medium (10 ml; containing $9.2 \times 10^7$ cells).

(c) Preparation of Myeloma Cells

Mouse myeloma cells P3U1 ($5 \times 10^6$ cells) were added to 25 ml of the following RPMI 1640 medium supplemented with fetal calf serum (hereinafter referred to as "RPMI medium") and thereto was added 8-azaguanine (100 μM). The cells were cultured under atmosphere containing 5% $CO_2$ at 37° C. for 5 days and washed with DMEM medium ($\times 2$) to prepare a suspension of the mouse myeloma cells P3U1 in DMEM (10 ml; containing $1.4 \times 10^8$ cells).

RPMI 1640 medium supplemented with fetal calf serum was prepared by adding distilled water to a mixture of RPMI 1640 (manufactured by GIBCO; 10.4 g), sodium hydrogen carbonate (1.3 g), L-glutamine (25.2 mg), penicillin G (63.5 mg), streptomycin sulfate (100 mg), tylosin (10 mg), 2-mercaptoethanol solution (manufactured by WAKO PURE CHEMICAL INDUSTRIES; 40 μl) and fetal calf serum (manufactured by FLOW Laboratories; 100 ml) to make a total amount of 1000 ml and passing through a 0.45 μm membrane filter (manufactured by TOYO ROSHI CO., LTD) for sterile filtration.

(d) Cell Fusion and Selection of Anti-HPV Antibody Producing Hybridomas

The suspension of the antibody producing spleen cells (10 ml; $9.2 \times 10^7$ cells) prepared in the above procedure (b) and the suspension of the myeloma cells P3U1 (0.66 ml; $9.2 \times 10^6$ cells) prepared in the above procedure (c) were mixed in a 50 ml centrifugation tube and the mixture was centrifuged at 1000 rpm for 10 minutes to precipitate the mixture of both cells. After removal of the supernatant, to the mixture of both cells was added dropwise DMEM medium (0.5 ml) containing PEG 1000 (42.5 w/w %) and DMSO (15%) while mildly stirring over a period of 1 minute. 1 ml, 1 ml, 5 ml, 5 ml and 10 ml of DMEM medium was then added dropwise in this order while mildly stirring at room temperature each over a period of 1 minute to fuse the cells. The treated mixture was then centrifuged at 1000 rpm for 10 minutes and the supernatant was removed to give a mixture of the fused cells.

For selection of hybridomas, the above mixture of the treated cells was suspended in HAT medium (RPMI medium comprising 100 μM hypoxanthine, 0.4 μM aminopterin and 16 μM thymidine) to prepare a cell suspension (104 ml, cell number: about $10^6$/ml).

The above cell suspension was then placed in a 96-well microplate (Falcon 3072 manufactured by FALCON) in an amount of 0.2 ml/well and the cells were cultured at 37° C. under atmosphere containing 5% $CO_2$. The cells were cultured for totally 10 days while replacing the whole supernatant in each well with fresh HAT medium (0.2 ml/well) on the fourth day so that the hybridomas can grow sufficiently.

The culture supernatant (hereinafter referred to as "culture supernatant (A)") in each well was then subjected to enzyme immunoassay as hereinbelow described to select anti-HPV antibody producing hybridomas.

Enzyme Immunoassay for Selection of Anti-HPV Antibody Producing Hybridomas:

The alkali-treated HPV-1 solution (104 μl) prepared in the above procedure (a) was diluted to a concentration of 1 μg/ml with 0.05M sodium carbonate-sodium hydrogen carbonate buffer (pH 9.6) and 100 μl of the diluted solution was poured into each well of 96-well microplate (Immulon 600 manufactured by Greiner Labortechnik) and allowed to stand at 4° C. overnight to fix the alkali-treated HPV-1 to the well. After washing each well with PBS (pH 7.4) containing 0.05% Tween-20 (polyoxyethylene sorbitan monolaurate) (hereinafter referred to as "T-PBS"), to the well was added PBS (pH 7.4; 300 μl) containing 0.5% (w/v) bovine serum albumin (manufactured by WAKO PURE CHEMICAL INDUSTRIES; hereinafter referred to as "BSA") and the mixture was allowed to stand at room temperature for 1 hour, followed by removal of the supernatant. Each of the above culture supernatant (A) was diluted twofold with PBS (pH 7.4) containing 0.1% (w/v) BSA and 100 μl thereof was added to each well at room temperature, and the mixture was reacted for 2 hours and washed with T-PBS (pH 7.4).

Biotin-labelled anti-mouse IgG+IgA+IgM (H+L) (manufactured by ZYMED Laboratories, Inc.) was diluted to a concentration of 5 μg/ml with PBS (pH 7.4) containing 0.1% (w/v) BSA, and 100 μl thereof was added to each well, and the mixture was reacted at room temperature for 1 hour and washed with T-PBS (pH 7.4).

Streptavidin peroxidase (manufactured by Amersham International PLC) was then diluted 1000-fold with PBS (pH 7.4) containing 0.1% (w/v) BSA, and 100 μl thereof was added to each well, and the mixture was reacted at room temperature for 30 minutes and washed with T-PBS (pH 7.4).

To each well was then added 100 μl of 0.15M citrate-sodium phosphate buffer (pH 5.0) containing 0.015% (w/v) hydrogen peroxide and o-phenylenediamine (0.2 mg/ml) as a substrate to react at room temperature for 5 minutes. 50 μl of 5N sulfuric acid was then added to each well to quench the reaction to give a test solution (hereinafter referred to as "test solution (T)").

On the other hand, the same procedures were repeated except that HAT medium was employed in place of the culture medium (A) to give a reference solution (hereinafter referred to as "test solution (C)").

Absorbance at 492 nm was measured for the above test solutions (A) and (C) using Corona 2 wave length microplate photometer (MTP-22, manufactured by CORONA ELECTRIC CO., LTD). Fifteen wells which contained the test solution (T) showing 0.1 or more higher absorbance than that of the test solution (C) were selected to obtain 15 kinds of anti-HPV antibody producing hybridomas.

(e) Cloning of Hybridomas and Selection of Hybridoma of the Invention

The above anti-HPV antibody producing hybridomas were cloned by a limiting dilution method.

The anti-HPV antibody producing hybridomas selected in the procedure (d) and BALB/c mouse thymus cells (obtained from BALB/c mouse of 6 weeks old by a conventional procedure) were suspended in HAT medium to prepare a suspension of mixed cells (concentration of hybridomas: 3 cells/ml, concentration of the thymus cells: about $3 \times 10^6$ cells/ml). 0.2 ml of the suspension was poured into each well of 96-well microplate (Falcon 3072) and the cells were cultured at 37° C. under atmosphere containing 5% $CO_2$ for 14 days. Those wells which produced one colony per well were selected and the culture supernatant thereof was subjected to enzyme immunoassay as in the above procedure (d) and three clones of hybridomas were selected which produced a monoclonal antibody having a high reactivity.

Three antibodies (designated K1H8, K3B5 and K4B2, respectively) produced by the above selected hybridomas were tested for their reactivity with the alkali-treated HPV-1 as described in the procedure (a) by the method described in the procedure (d). The results are shown in Table 2 with the absorbance ($A_{492}$)

TABLE 2

| Antibody | Reactivity (absorbance $A_{492}$) |
|---|---|
| K1H8 | 0.89 |
| K3B5 | 0.81 |
| K4B2 | 0.72 |
| Control | 0.01 |

In order to select hybridomas which produce monoclonal antibodies reactive with various HPVs for these three clones, they were tested for the antigen-antibody reaction with a plurality of HPV-infected tissues in accordance with the test method described in Experiment. Among three clones, the antibody (K1H8) from one clone reacted all of these tissues tested, and hence, this hybridoma was selected.

The hybridoma producing this antibody K1H8 was grown in the manner described hereinbelow and deposited under accession number FERM BP-2278 as mentioned hereinbefore.

EXAMPLE 2

(Preparation of Monoclonal Antibody)

The anti-human papillomavirus monoclonal antibody (K1H8) was prepared from the hybridoma culture supernatant.

The above "anti-human papillomavirus monoclonal antibody (K1H8) producing hybridomas" ($10^5$ cells) in HAT medium were transferred into HT medium (RPMI medium containing 100 μM hypoxanthine and 16 μM thymidine; 5 ml) and subcultured at 37° C. under atmosphere containing 5% $CO_2$ for 14 days, and then transferred into RPMI medium (100 ml) and cultured at 37° C. under atmosphere containing 5% $CO_2$ for 14 days.

The hybridomas were separated and removed by centrifugation (1000 rpm, 10 minutes) to give the culture supernatant (100 ml). To the supernatant was added a saturated aqueous solution of ammonium sulfate (66.7 ml), the mixture was stirred at room temperature for 1 hour, allowed to stand at the same temperature for 1 hour, centrifuged (10,000 rpm) at 4° C. for 20 minutes and the supernatant was discarded to give precipitate.

To the precipitate was added 0.9% (w/v) physiological saline solution (100 ml) to dissolve and the solution was centrifuged (10,000 rpm, 20 minutes) at 4° C. to give supernatant. To the supernatant was added a saturated aqueous solution of ammonium sulfate (50.0 ml), and the mixture was stirred at room temperature for 1 hour, allowed to stand at the same temperature for 1 hour, centrifuged (10,000 rpm, 20 minutes) at 4° C. and the supernatant was discarded to give precipitate.

The obtained precipitate was dissolved in PBS (100 ml) and the solution was dialyzed against PBS (5 liters) at 4° C. for 16 hours to give a solution of the anti-human papillomavirus monoclonal antibody (K1H8) in PBS (100 ml, concentration: 23.5 μg/ml).

The antigen analysis test (A) described hereinbelow proved that this monoclonal antibody had characteristics capable of inducing antigen-antibody reaction with polypeptides of about 57 kilodaltons, about 160 kilodaltons and about 230 kilodaltons of HPV-1.

Further, the immunological classification test (B) described hereinbelow proved that this antibody belonged to immunoglobulin subclass $G_1$ and the L chain thereof had isotype of κ chain.

(A) Antigen Analysis Test of Anti-human Papillomavirus Monoclonal Antibody (K1H8)

The HPV-1 purified in Example 1-(a) was diluted to a concentration of 10 μg/ml and subjected to SDS-polyacrylamide gel electrophoresis in accordance with the procedure by Laemmli (see Nature, Vol. 227, pp680, 1970). After electrophoresis, polyvinylidene fluoride membrane (manufactured by Millipore) was put on the gel and electrophoresis was further conducted in a transfer buffer (comprising 20% methyl alcohol, 25 mM Tris(hydroxymethyl)aminomethane-HCl, and 192 mM glycine, pH 8.3) at 4° C. and at 15 V for 16 hours for transcription. After transcription, the polyvinylidene fluoride membrane was added to PBS (pH 7.4; 10 ml) containing 5% (w/v) BSA, and the mixture was subjected to blocking at 37° C. for 1 hour.

A solution of the monoclonal antibody (K1H8) was prepared at a concentration of 1 μg/ml with PBS (pH 7.4) containing 1% (w/v) BSA, and to 10 ml of this solution was added the above blocked polyvinylidene fluoride membrane and the mixture was incubated at 37° C. for 2 hours, followed by washing (×5) with T-PBS (pH 7.4) each for 5 minutes to give monoclonal antibody (K1H8)-reacted polyvinylidene fluoride membrane.

Then, to a solution (10 ml) of biotin-labelled anti-mouse IgG+IgA+IgM (H+L)(manufactured by ZYMED Laboratories, Inc.) diluted to a concentration of 5 μg/ml with PBS (pH 7.4) containing 1% (w/v) BSA was added the above polyvinylidene fluoride membrane, and the mixture was incubated at 37° C. for 1 hour, followed by washing (×5) with the same T-PBS (pH 7.4) as above to give biotin-labelled anti-mouse IgG+IgA+IgM (H+L)-reacted polyvinylidene fluoride membrane.

To a solution (10 ml) of streptavidin peroxidase (manufactured by Amersham International PLC) diluted to 1000-fold with PBS containing 1% (w/v) BSA was then added the above polyvinylidene fluoride membrane, and the mixture was incubated at 37° C. for 30 minutes, followed by washing (×5) with T-PBS (pH 7.4) each for 5 minutes to give streptavidin peroxidase-reacted polyvinylidene fluoride membrane.

The above polyvinylidene fluoride membrane was then added to PBS (pH 7.4; 10 ml) containing 3,3'-diaminobenzidine.4HCl (0.2 mg/ml) and 0.015% (w/v) hydrogen peroxide, and the mixture was reacted at room temperature for 10 minutes. After the reaction was quenched with distilled water, the polyvinylidene fluoride membrane was dried with a drier to reveal bands of polypeptides of HPV-1 reacted with the monoclonal antibody (K1H8).

Each molecular weight of the polypeptides of HPV-1 reacted with the monoclonal antibody (K1H8) was determined with commercially available molecular weight markers (catalogue No. 17-0445-01 manufactured by Pharmacia and catalogue No. 161-0305 manufactured by Bio-Rad) in the following manner.

That is, the commercially available molecular weight markers were subjected to the same SDS-polyacrylamide gel electrophoresis as above and transcribed onto polyvinylidene fluoride membrane, followed by staining with an aqueous solution containing 0.25% (w/v) Coomassie Brilliant Blue R 250, 45% ethanol and 45% acetic acid at room temperature for 10 minutes. The membrane was then decolorized with 90% aqueous ethanol solution at room temperature for 5 minutes and bands of the molecular weight marker polypeptides were observed. A migrating distance of each band was then measured to give a relative mobility. A molecular weight of each HPV-1 polypeptide reacted with the above monoclonal antibody (K1H8) was determined from a relative mobility of each band of the HPV-1 polypeptides.

(B) Immunological Classification Test

In order to determine the class, subclass and isotype of the L chain of the above monoclonal antibody (K1H8), the following procedures were performed.

That is, rabbit antibodies against each class and subclass of mouse immunoglobulin (IgA, IgM, IgG$_1$, IgG$_{2a}$, IgG$_{2b}$ and IgG$_3$) and rabbit anti-mouse L chains (κ chain and λ chain) antibodies (manufactured by Miles Laboratories, Inc.) were used to prepare solutions in 0.05M sodium carbonate-sodium hydrogen carbonate buffer (pH 9.6), each solution containing 5 μg/ml of one of the antibodies. 100 μl of the solutions was poured into each well of 96-well microplate (Immulon 600) and the wells were allowed to stand at 4° C. overnight for fixation. After washing each well with T-PBS (pH 7.4), PBS (pH 7.4; 300 μl) containing 0.5% (w/v) BSA was added to each well and allowed to stand at room temperature for 1 hour, followed by removal of the supernatant.

Then, the monoclonal antibody (K1H8) solution (0.5 ml) obtained above was diluted twofold with PBS (pH 7.4) containing 0.1% (w/v) BSA and 100 μl of the solution was added to each well, and the mixture was reacted at room temperature for 2 hours, followed by washing with T-PBS (pH 7.4).

100 μl of a solution of biotin-labelled anti-mouse IgG+IgA+IgM (H+L)(manufactured by ZYMED Laboratories, Inc.) diluted to a concentration of 5 μg/ml with PBS (pH 7.4) containing 0.1% (w/v) BSA was then added to each well, and the mixture was reacted at room temperature for 1 hour, followed by washing with T-PBS (pH 7.4).

100 μl of streptavidin peroxidase (manufactured by Amersham International PLC) diluted 1000-fold with PBS (pH 7.4) containing 0.1% (w/v) BSA was then added to each well, and the mixture was reacted at room temperature for 30 minutes, followed by washing with T-PBS (pH 7.4).

Then, to each well was added 100 μl of 0.15M citrate-sodium phosphate buffer (pH 5.0) containing 0.015% (w/v) hydrogen peroxide and o-phenylenediamine (0.2 mg/ml) as a substrate, and the mixture was reacted at room temperature for 5 minutes.

To each well was then added 50 μl of 5N sulfuric acid to quench the reaction. Absorbance at 492 nm was measured for the above reaction solutions with Corona 2 wave length microplate photometer (MTP-22 manufactured by CORONA ELECTRIC CO., LTD) to assess the reactivity of the monoclonal antibody (K1H8) of the invention with each immunoglobulin. The highest reactivity of the anti-human papillomavirus monoclonal antibody (K1H8) with rabbit anti-mouse IgG$_1$ antibody and rabbit anti-mouse κ antibody proved that the anti-human papillomavirus monoclonal antibody (K1H8) belonged to immunoglobulin subclass G$_1$ wherein isotype of L chain is a κ chain.

EXAMPLE 3

The hybridoma was grown in the peritoneal cavity of a mouse and the anti-human papillomavirus monoclonal antibody (K1H8) was obtained from ascites.

Pristane (2,6,10,14-tetramethylpentadecane; 0.5 ml) was intraperitoneally administered to a BALB/c mouse 9 weeks old. Twenty one days after the administration, anti-human papillomavirus monoclonal antibody (K1H8) producing hybridomas, which were prepared by culturing the anti-human papillomavirus monoclonal antibody (K1H8) producing hybridomas prepared in Example 1 in HT medium in the manner described in Example 2 followed by subculture in RPMI medium, were suspended in RPMI medium (concentration: about 2×10$^7$ cells/ml) and 0.5 ml of the suspension was intraperitoneally administered to the animal.

Ascites produced (about 10 ml) was then taken out and subjected to centrifugation (1000 rpm, 10 minutes) to precipitate cellular components to give supernatant (7.4 ml). To the supernatant was added a saturated aqueous solution of ammonium sulfate (4.9 ml) and the mixture was stirred at room temperature for 1 hour, allowed to stand at the same temperature for 1 hour, subjected to centrifugation (10,000 rpm, 20 minutes) at 4° C. and the supernatant was discarded to give precipitate.

To the precipitate was added 0.9% (w/v) physiological saline solution (7.4 ml) to dissolve and the solution was subjected to centrifugation (10,000 rpm, 20 minutes) at 4° C. to give supernatant. To the supernatant was added a saturated aqueous solution of ammonium sulfate (3.7 ml) and the mixture was stirred at room temperature for 1 hour, allowed to stand at the same temperature for 1 hour, subjected to centrifugation (10,000 rpm, 20 minutes) at 4° C. and the supernatant was discarded to give precipitate.

The precipitate was dissolved in PBS (7.4 ml) and the solution was dialyzed against PBS (3000 ml) at 4° C. for 16 hours to give a solution of the anti-human papillomavirus monoclonal antibody (K1H8) in PBS (7.4 ml, concentration: 7.01 mg/ml). The thus obtained monoclonal antibody showed the same reactivity against the polypeptides of HPV-1 as that of the monoclonal antibody prepared in Example 2.

What is claimed is:

1. An anti-human papillomavirus (HPV) monoclonal antibody which is produced by a hybridoma deposited under the accession number FERM BP-2278.

2. A hybridoma deposited under the accession number FERM BP-2278.

* * * * *